United States Patent [19]

Ikeda et al.

[11] Patent Number: 4,657,847

[45] Date of Patent: Apr. 14, 1987

[54] SILVER HALIDE PHOTOGRAPHIC LIGHT-SENSITIVE MATERIALS

[75] Inventors: Hideo Ikeda, Minami-ashigara; Shigeru Ohno, Odawara; Koki Nakamura; Nobuaki Miyasaka, both of Minami-ashigara, all of Japan

[73] Assignee: Fuji Photo Film Co., Ltd., Kanagawa, Japan

[21] Appl. No.: 765,238

[22] Filed: Aug. 13, 1985

[30] Foreign Application Priority Data

Aug. 16, 1984 [JP] Japan .................. 59-170588

[51] Int. Cl.$^4$ .............................. G03C 1/34
[52] U.S. Cl. .................... 430/523; 430/502; 430/603; 430/611; 430/445
[58] Field of Search ............ 430/603, 611, 502, 523, 430/264, 267, 445

[56] References Cited

U.S. PATENT DOCUMENTS

| | | | |
|---|---|---|---|
| 3,017,270 | 1/1962 | Tregillus et al. | 430/248 |
| 3,305,362 | 2/1967 | Riester et al. | 430/611 |
| 3,397,987 | 8/1968 | Luckey et al. | 430/603 |
| 4,393,128 | 7/1983 | Shiba et al. | 430/611 |
| 4,604,339 | 8/1986 | Sugimoto et al. | 430/611 |

Primary Examiner—Won H. Louie

Attorney, Agent, or Firm—Burns, Doane, Swecker & Mathis

[57] ABSTRACT

A silver halide photographic light-sensitive material comprising a support having coated thereon at least one silver halide emulsion layer and a surface protecting layer, said silver halide photographic light-sensitive material comprising photosensitive silver halide grains and internally fogged silver halide grains, said internally fogged silver halide grains having adsorbed thereon at least one compound represented by the formula (I):

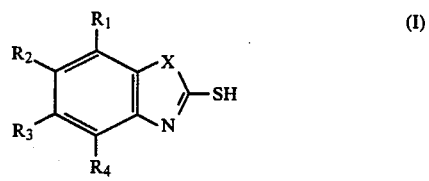

wherein X represents —O—, —NH— or —S—, $R_1$, $R_2$, $R_3$ and $R_4$ represent hydrogen atom or a substituent, and at least one of $R_1$, $R_2$, $R_3$ and $R_4$ is substituted or unsubstituted alkyl or aryl group having up to 13 carbon atoms, which is bonded directly or through a divalent linkage group, to the aromatic nucleus.

15 Claims, No Drawings

SILVER HALIDE PHOTOGRAPHIC LIGHT-SENSITIVE MATERIALS

BACKGROUND OF THE INVENTION (1) Field of the Invention

This invention relates to novel silver halide photographic light-sensitive materials and, more particularly, to high-speed silver halide photographic light-sensitive materials which give an image having high contrast and high maximum density.

(2) Description of the prior art

As regards photographic silver images, the ratio of the optical density of the image to the amount of silver constituting the image per unit area is generally called the covering power. This covering power is used as a measure of the optical efficiency of the image-constituting silver. Generally, the smaller the size of the silver halide grains becomes, the greater the covering power of the photographic light-sensitive emulsion layer containing the silver halide grains becomes. On the contrary, since the greater the size of the silver halide grains becomes, the higher the sensitivity or speed of the silver halide emulsion, an emulsion containing silver halide grains of a large size is used in making a high-speed photographic light-sensitive material. It is therefore necessary to use a larger amount of silver per unit area so as to obtain a high-speed photographic light-sensitive material which gives a certain image density.

In other words, to attain both high sensitivity and maximum image density, the photographic light-sensitive material must contain a larger amount of silver salts per unit area thereof. This has been one of the problems in making a high-speed photographic light-sensitive material.

As an attempt to improve the covering power while maintaining a high sensitivity, it has been proposed to add various polymers to a high-speed emulsion containing coarser silver halide grains, as described in British Pat. Nos. 1,048,057 and 1,039,471, and U.S. Pat. Nos. 3,043,697 and 3,446,618. All the methods of these patents give only a slight and insufficient increase in covering power and further have a disadvantage in that they decrease the strength of the coated film layer. When the photographic light-sensitive material having such weak film layer is processed after imagewise exposure through an automatic developing processor of the type commonly used at present, gelatin contained in the layer partly dissolves into the developing solution or the fixing solution, sticks to the conveyor roller of the automatic developing processor, and transfers to the photographic material to produce stains on the photographic image.

U.S. Pat. Nos. 2,996,382 and 3,178,282 disclose high-speed silver halide photographic light-sensitive materials comprising surface latent image type silver halide coarse grains and internally fogged silver halide fine grains incorporated in the same or adjacent emulsion layers, which give a photographic image having increased contrast and covering power. However, these photographic light-sensitive materials tend to be fogged during development. Further they have a disadvantage in that irregular stains are produced on the photographic materials when they are processed in a developing bath and subsequently in a fixing bath without being processed in an intermediate stopping bath, using an automatic developing processor. The problem of irregular stains seems to partly originate from the formation of fog which is caused partly by the careless incorporation of the fixing solution into the developing solution.

As regards the problem of the susceptibility to fogging in the developing process, U.S. Pat. No. 3,397,987 discloses a method for decreasing the fog formation in photographic elements, especially those sensitized with onium salts or polyalkyleneoxides, which comprises adsorbing on internally fogged silver halide grains, the development antifoggant heterocyclic nitrogen compounds containing a mercapto group which is linked to the carbon atom at α-position with respect to the nitrogen atom of the hetero ring, in the methods as described in U.S. Pat No. 2,996,382 and 3,178,282.

However, almost none of the compounds disclosed in U.S. Pat No. 3,397,987 have a good effect on the problem of the irregular stains produced in the processing by an automatic developing processor. Among these compounds, only 1-(3-capramido)-phenyl-5-mercaptotetrazole and 1-(3-pelargonamido)-phenyl-5-mercaptoterazole had an improving effect on the problem of the irregular stains but they had a disadvantage in that the sensitivity of the photographic materials decreased with time under conditions of high temperature and humidity.

SUMMARY OF THE INVENTION

Accordingly, an object of this invention is to provide high speed silver halide photographic light-sensitive materials which give an image having high contrast and high maximum density.

Another object of this invention is to provide silver halide photographic light-sensitive materials which are resistant to fogging when they are processed after imagewise exposure in the developing process, which do not produce irregular stains on the image surface when they are processed in a developing bath and subsequently in a fixing bath without being processed in an intermediate stopping bath, using an automatic developing processor, and which suffer little loss of good photographic properties after being stored under conditions of high temperature and humidity.

The objects of this invention can be attained by a silver halide photographic light-sensitive material comprising a support having coated thereon at least one silver halide emulsion layer and a surface protecting layer, said silver halide photographic light-sensitive material comprising photosensitive silver halide grains and internally fogged silver halide grains, said internally fogged silver halide grains having adsorbed thereon at least one compound represented by the formula (I):

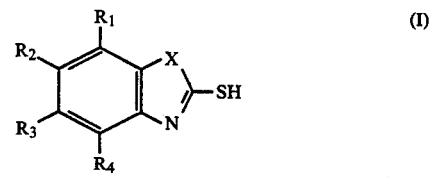

In the formula (I), X represents —O—, —NH— or —S—. Preferably, X is —NH—. $R_1$, $R_2$, $R_3$ and $R_4$ represent hydrogen atom or a substituent group. Preferably, $R_1$, $R_2$, $R_3$ and $R_4$ represent hydrogen, halogen atom (e.g., F, Cl, Br etc.), substituted or unsubstituted alkyl (e.g. methyl, trifluoromethyl, ethyl, n-octyl, benzyl, etc.), substituted or unsubstituted aryl (e.g., phenyl, p-chlorophenyl, etc.), substituted or unsubstituted alkoxy, aryloxy, (e.g., methoxy, n-hexyloxy, phenoxy, n-octyloxy, 2-ethylhexyloxy, etc.), sulfonyl (e.g., methanesulfonyl, p-toluenesulfonyl, etc.), sulfonamido (e.g., n-octanesulfonamido, p-toluenesulfonamido, etc.) sulfamoyl (diethylsulfamoyl, 4-chlorophenylsulfamoyl, etc.), carbamoyl (e.g., n-butylcarbamoyl, 4-cyanophenylcarbamoyl, 2-ethylhexylcarbamoyl, etc.), amido (e.g., n-hexaneamido, n-decaneamido, benzamido, 2-ethylhexanoylamino, etc.), ureido (e.g., 3-butylureido, morpholinocarbonylamino, etc.), arylcarbonylamino, aryloxycarbonylamino (e.g. phenoxy carbonylamino), alkylcarbonylamino (e.g. iso-butylcarbonylamino), alkoxycarbonylamino (e.g. ethoxycarbonylamino), arylcarbonyl, aryloxycarbonyl (e.g. phenoxycarbonyl), alkylcarbonyl, alkoxycarbonyl (e.g. ethoxycarbonyl), aryl or alkylaminocarbonyloxy (e.g., phenylaminocarbonyloxy, isobutylaminocarbonyloxy, etc.), cyano, and alkyl or arylthio (e.g., n-octylthio, 2-methoxycarbonylphenylthio, etc.). These substituents are preferably those having up to 13, particularly up to 11 carbon atoms. At least one of $R_1$, $R_2$, $R_3$ and $R_4$ is substituted or unsubsituted alkyl or aryl having up to 13 carbon atoms, preferably substituted or unsubstituted alkyl having 5 to 11 carbon atoms, which is bonded, directly or through a divalent linkage group, to the aromatic nucleus. Examples of suitable divalent linkage groups include amido, sufonamido, ureido, ether, thioether, sulfonyl, carbonyl, urethane, carbamoyl and sulfamoyl linkages.

DETAILED DESCRIPTION OF THE INVENTION

Typical Examples of compounds which can be used in this invention include the following to which this invention is not restricted.

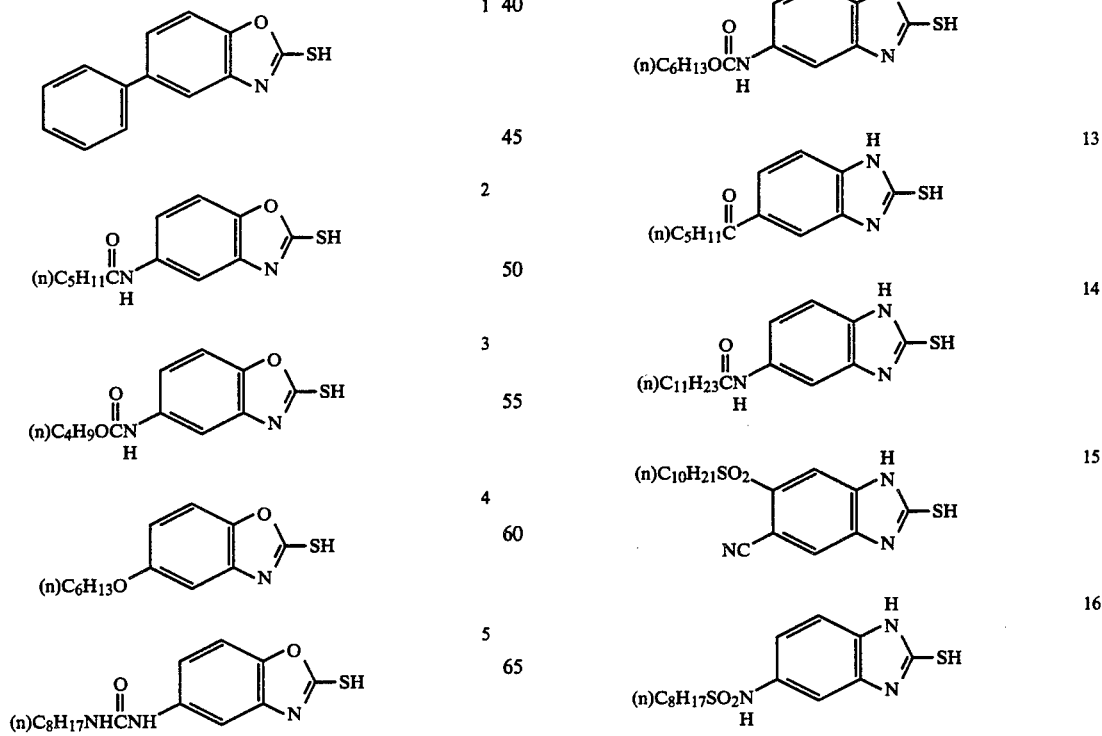

-continued
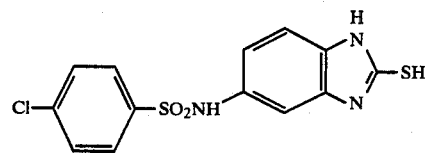 17
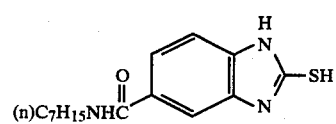 18
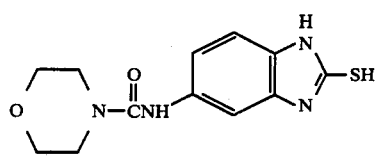 19
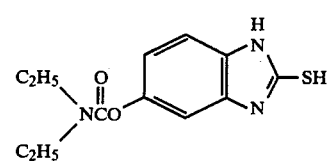 20
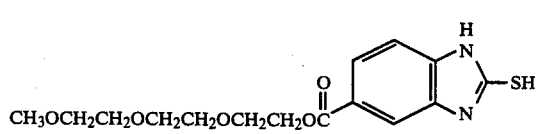 21
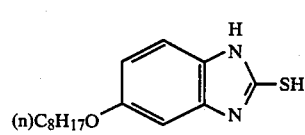 22
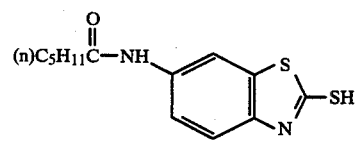 23
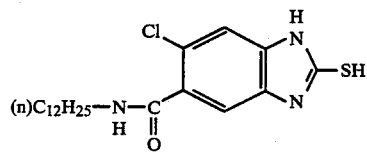 24
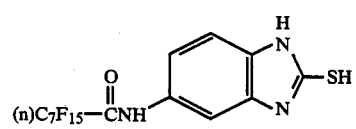 25
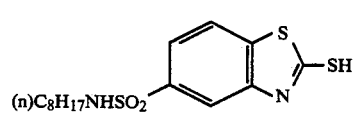 26
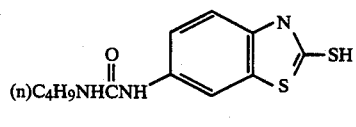 27
-continued
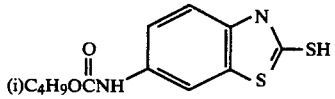 28
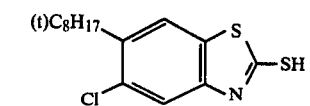 29
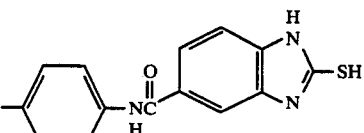 30
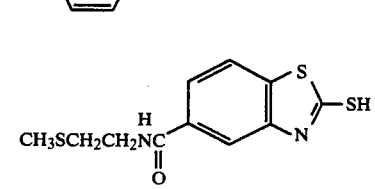 31
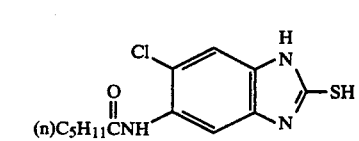 32
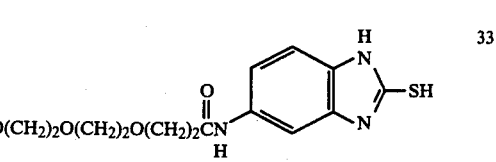 33
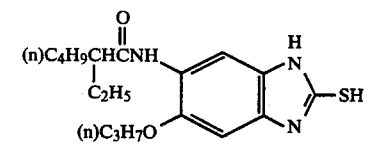 34
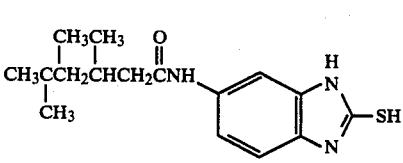 35
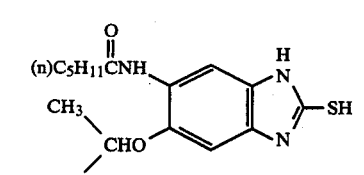 36
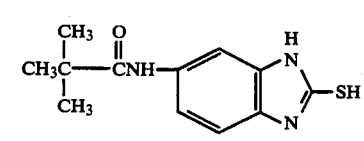 37
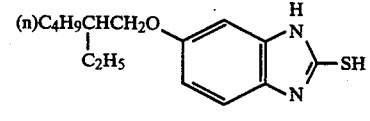 38

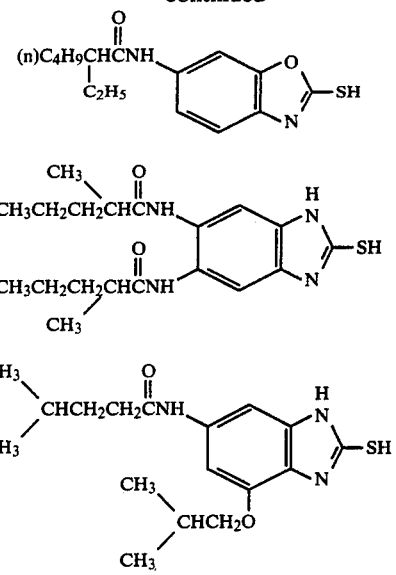

The compounds represented by the formula (I), which can be used in this invention, can be prepared according to the method as described in J. Van Allan. B. D. Deacon, Org. Synth., IV. 569 (1963), J. Bunner Ber., 9, 465 (1876), L. B. Sebrell, C. E. Boord, J. Am. Chem. Soc., 45, 2390 (1923) or the following typical synthetic examples.

SYNTHETIC EXAMPLE 1

Synthesis of Compound 10

5-Amino-2-mercaptobenzimidazole (8.3 g) was dissolved in pyridine (120 ml), to which hexanoylchloride (6.7 g) was dropwise added under ice-cooled condition. The mixture was stirred for 2 hours at room temperature, and poured into ice-water (800 ml). The precipitated crystal was filtered and recrystallized from a mixed solvent of ethanol and water to obtain Compound 10 as a crystal. Yield 7.8 g, m.p. 262°–264° C. (dec.).

SYNTHETIC EXAMPLE 2

Synthesis of Compound 14

5-Amino-2-mercaptobenzimidazole (8.3 g) was dissolved in pyridine (120 ml), to which lauroylchloride (12 g) was dropwise added under ice-cooled condition. The mixture was stirred at room temperature for 3 hours, and poured into ice-water (800 ml). The precipitated crystal was filtered and recrystallized from a mixed solvent of methanol and water. Yield 10.2 g. m.p. 266°–267° C. (dec.).

SYNTHETIC EXAMPLE 3

Synthesis of Compound 18

5-Carboxy-2-mercaptobenzimidazole (5.8 g) was added to dimethylformamide (60 ml), to which triethylamine (6.3 ml) and subsequently ethyl chloroformate (4.3 ml) were dropwise added under ice-cooled condition. The mixture was stirred for 30 minutes under ice-cooled condition and then heptylamine (5.2 g) was dropwise added and stirred for 4 hours. The reaction mixture was poured into a solution of sodium bicarbonate (3 g) in water (500 ml) to precipitate Compound 18, followed by recrystallization from ethylacetate. Yield 3.8 g. m.p. 230°–232° C.

SYNTHETIC EXAMPLE 4

Synthesis of Compound 22 p-Octyloxy-o-phenylenediamine (4.7 g) was added to a solution of potassium hydroxide (1.2 g) in ethanol (60 ml), to which carbon disulfide (6 ml) was dropwise added to 50° C. The mixture was refluxed for 4 hours and poured into ice-water (150 ml), to which concentrated hydrochloric acid (3 ml) was added. The precipitate was filtered, followed by recrystallization from acetonitrile to obtain Compound 22. Yield 3.7 g. m.p. 230°–232° C.

SYNTHETIC EXAMPLE 5

Synthesis of Compound 23

6-Amino-2-mercaptobenzthiazole (9.1 g) was added to pyridine (70 ml), to which hexanoylchloride (6.7 g) was dropwise added under ice-cooled condition. The mixture was stirred at room temperature for 3 hours and poured into ice-water (800 ml). The precipitated crystal was filtered, followed by recrystallization from a mixed solvent of ethanol and water. Yield 6.9 g. m.p. 179°–180° C.

The compounds represented by the formula (I) may be used in this invention in an amount of $1 \times 10^{-5}$ to $1 \times 10^{-1}$ mole, preferably $1 \times 10^{-4}$ to $1 \times 10^{-2}$ mole per mole of internally fogged silver halide grains. Most preferably, the compounds are used in nearly saturated adsorption on the surface of the internally fogged silver halide grains. The compounds may be added directly to the hydrophilic colloid to be dispersed therein or may be added after dissolved in such an organic solvent as methanol, ethyleneglycol, etc.

In a case where the internally fogged silver halide emulsion and the photosensitive silver halide emulsion are to be contained in the same emulsion layer, it is preferred that the compounds of the formula (I) be added to the internally fogged silver halide emulsion to be adsorbed thereon before the latter is mixed with the photosensitive silver halide emulsion.

The term "photosensitive" used in this specification means that the sensitivity of the photosensitive silver halide emulsion is higher than that of the internally fogged silver halide emulsion, more specifically, more than 10 times, preferably 100 times higher than that of the latter emulsion. The term "sensitivity" used herein is defined below.

The photosensitive silver halide emulsion which can be used in this invention can be any conventional silver halide emulsion, e.g., the surface latent image type emulsion.

The surface latent image type emulsion used in this specification means such emulsions that the sensitivity thereof obtained by the surface development (A) described below after exposure for 1 to 1/100 second is higher, preferably more than 2 times higher than that obtained by the internal development (B) described below.

Sensitivity is defined as follows:

$$S = 100/Eh$$

wherein S is sensitivity and Eh is the exposure value required for obtaining the average of the maximum density (Dmax) and the minimum density (D min.), that is, ½ (Dmax+Dmin).

Surface developent (A)

Developing is done at 20° C. for 10 minutes in a developing bath of the following composition:

| N—Methyl-p-aminophenol (hemi sulfate) | 2.5 g |
|---|---|
| Ascorbic acid | 10 g |
| Sodium metaborate tetrahydrate | 35 g |
| Potassium bromide | 1 g |
| Water to | 1 l |

Internal development (B)

After treatment in a bleaching bath containing ferricyanide (3 g/l) and phenosafranine (0.0126 g/l) at about 20° C. for 10 minutes, developing is done at 20° C. for 10 minutes in a developing bath of the following composition:

| N—Methyl-p-aminophenol (hemi sulfate) | 2.5 g |
|---|---|
| Ascorbic acid | 10 g |
| Sodium metaborate tetrahydrate | 35 g |
| Potassium bromide | 1 g |
| Sodium thiosulfate | 3 g |
| Water to | 1 l |

Specific examples of the surface latent image type silver halides which can be used in this invention include silver chloroiodide, silver bromoiodide, silver chloride, silver bromochloride, silver bromide and silver bromochloroiodide. Among these, silver bromide or silver bromoiodide is preferred. Th amount of silver iodide is preferably in the range of 0 to 30 mole %, especially 0.5 to 10 mole %. The average size of the surface latent image type silver halide grains is preferably greater than that of the internally fogged silver halide grains, especially not less than 0.6 micron.

The size distribution of the silver halide grains may be narrow or broad. The silver halide grains in the emulsions may be of regular crystal form such as cubic or octahedral, of irregular crystal form such as spherical or tabular, or of complex crystal form. The silver halide grains may be a mixture of different crystal form grains. The tabular silver halide grains having a diameter-to-thickness ratio of five or more may suitably be used in this invention. This type of tabular silver halide grains are in detail described in U.S. Pat. Nos. 4,434,226 and 4,434,227 and Japanese Patent Public Disclosure No. 127921/1983.

The photographic emulsion which can be used in this invention may be prepared by the methods described in, e.g., P. Glafkides, Chimie et Physique Photographique (Paul Montel 1967); G. F. Duffin, Photographic Emulsion Chemistry (The Focal Press. 1966); and V. L. Zelikman et al, Making and Coating Photographic Emulsion (The Focal Press. 1964), that is, by any of an acidic process, a neutral process, an ammonia process, etc. Reaction between a soluble silver salt and a soluble halide salt may be carried out by any of single jet method, double jet method and a combination thereof.

A process for the formation of grains in the presence of excess silver ion (the so-called reverse mixing process) may also be used. A process in which a pAg in a liquid phase in which silver halide is formed is kept constant, which is one of the simultaneous mixing processes and which is the so-called controlled double jet process, can be used. According to this process, silver halide grains having regular crystal form and nearly uniform grain size (mono-dispersed emulsion) can be obtained. A mixture of two or more kinds of silver halide grains which have been separately or differently prepared may be used.

During the formation or physical ripening of silver halide grains, there may be allowed to coexist cadmium salts, zinc salts, lead salts, thallium salts, iridium salts or complex salts thereof, rhodium salts or complex salts thereof, iron salts or complex salts thereof, etc.

It is usual to remove soluble salts from the silver halide emulsions used in this invention after the formation or physical ripening of the silver halide grains. For this purpose, there may be used the traditional Noodle washing process in which the removal of soluble salts is carried out by gelling gelatin or a flocculation method using inorganic salts of polyanion, e.g., sodium sulfate, anionic surface active agents, anionic polymers (e.g. polystyrene sulfonic acid), or gelatin derivatives (e.g., aliphatic acylated gelatin, aromatic acylated gelatin, aromatic carbamoylated gelatin, etc.). The removal step of soluble salts may be omitted.

The photosensitive silver halide emulsions are usually chemically sensitized although a non-sensitized emulsion called the primitive emulsion may also be used in this invention. For the chemical sensitization, there may be used the methods as described in the book written by Glafkides or Zelikman et al mentioned earlier, or H. Frieser, Die Grundlagen der Photographischen Prozesse mit Silverhalpgeniden (Akademische Verlagsgesellshaft. 1968). Namely, sulfur sensitization using a sulfur-containing compound which can react with silver ion or active gelatin, reduction sensitization using a reducing compound, noble metal sensitization using noble metal such as gold, etc. may be used alone or in a combination. As sulfur sensitizers, there may be used thiosulfates, thioureas, thiazoles, rhodanines, etc., specific examples of which are described in U.S. Pat. Nos. 1,574,944; 2,410,689; 2,278,947; 2,728,668; 3,656,955; 4,032,928; and 4,067,740.

As reduction sensitizing agents, there may be used stannous salts, amines, hydrazine derivatives, formamidinesulfinic acid, silane compounds, etc., specific examples of which are described in U.S. Pat. Nos. 2,487,850; 2,419,974; 2,518,698; 2,983,609; 2,983,610; 2,694,637; 3,930,867; and 4,054,458.

For the purpose of the noble metal sensitization, there may be used, in addition to gold complex salts, other complex salts of the metals of Group VIII of the periodic table, e.g., platinum, iridium, palladium, etc., specific examples of which are described in U.S. Pat. Nos. 2,399,083 and 2,448,060; British Pat. 618,061; etc.

Various hydrophilic colloids can be used as a binder in the photographic light-sensitive materials of this invention. Examples of such colloids include hydrophilic colloids commonly used in the photographic field, such as, gelatin, colloidal albumin, polysaccharides, cellulose derivatives, synthetic resins, e.g., polyvinyl compounds including polyvinyl alcohol derivatives, polyacrylamides, etc. In combination with the hydrophilic colloids, there may be contained in the photographic elements of this invention, hydrophobic colloids, especially those capable of increasing the dimension stability of the elements. Examples of such hydrophobic colloids include water-insoluble polymers prepared by the polymerization of such vinyl monomer as alkyl acrylates, alkyl methacrylates, acrylic acid, sulfoalkyl acrylates, sulfoalkyl methacrylates, etc.

Various compounds may be added to the photographic emulsion used in this invention in order to prevent the reduction of sensitivity or formation of fog during the manufacture, storage or processing of the photographic elements. Examples of such compounds commonly known in the art include 4-hydroxy-6-methyl-1,3,3a,7-tetraazaindene, 3-methyl-benzthiazole, 1-phenyl-5-mercaptotetrazole, other heterocyclic compounds, mercury-containing compounds, other mercapto compounds, metal salts, etc. Specific examples of such compounds are described in K. Mees, "The Theory of the Photographic Processes" 3rd. ed. (1966) in which many references are made to earlier works, and further described in U.S. Pat. Nos. 1,758,576; 2,110,178; 2,131,038; 2,173,628; 2,697,040; 2,304,962; 2,324,123; 2,394,198; 2,444,605; 2,444,606; 2,444,607; 2,444,608; 2,566,245; 2,694,716; 2,697,099; 2,708,162; 2,728,663; 2,728,664; 2,728,665; 2,476,536; 2,824,001; 2,843,491; 2,886,437; 3,052,544; 3,137,577; 3,220,839; 3,226,231; 3,236,652; 3,251,691; 3,252,799; 3,287,135; 3,326,681; 3,420,668; and 3,622,339; and British Pat. Nos. 893,428; 403,789; 1,173,609; and 1,200,188.

The emulsion used in the photographic materials of this invention, in which silver halide grains containing internal fog centers are incorporated, is such that when a test piece prepared by coating the emulsion on a transparent support in an amount of 2 g/m$^2$ based on the silver amount is developed in the developing agent D-19 (designated by EASTMAN KODAK COMPANY) at 35° C. for 2 minutes without exposure, it gives 0.5 or less of a transmission fog density (exclusive of the density of the support itself) and when it is developed in the developing agent D-19 to which potassium iodide has been added in an amount of 0.5 g/l, at 35° C. for 2 minutes without exposure, it gives 1.0 or more of a transmission fog density (exclusive of the density of the support itself).

The emulsions in which silver halide grains containing internal fog centers are incorporated can be prepared by various known methods. Examples of such methods include a process as described in U.S. Pat. No. 2,996,382 in which an emulsion having high internal photosensitivity as described in U.S. Pat. No. 2,592,250 is fogged by photo-irradiation; a process as described in Japanese Patent Public Disclosure No. 215647/1983, in which silver halide grains are fogged under conditions of a low pAg and a high pH, or are chemically fogged by reducing agents, gold compounds, sulfur-containing compounds, etc. to prepare core grains containing fog centers, followed by the deposition of silver halide on the core surface to prepare shells around the core grains (see the technique for the preparation of a core-shell type grains emulsion as described in U.S. Pat. No. 3,206,313); or a process in which silver halide grains are internally and surface fogged, followed by the bleaching of fog centers on the grain surface by a ferricyanide solution, etc.

The average size of the silver halide grains containing internal fog centers is smaller than that of the surface latent image type silver halide grains and is preferably 1.0 to 0.05 micron, more preferably 0.6 to 0.1 micron, and most preferably less than 0.5 micron, the grains of such average size giving good results.

The term "size of silver halide grains" used in this specification means the diameter of the grains if they are in the form of a true or near sphere, or the diameter of a sphere having the same volume as that of the grains if they are in other forms (e.g. cubic, tubular, etc.).

Internally fogged silver halide grains may be of any of silver bromide, silver bromochloride, silver bromochloroiodide, silver bromochloride, silver chloride, etc.

The weight ratio of the photosensitive silver halide grains to the internally fogged silver halide grains to be incorporated in the silver halide photographic light-sensitive materials of this invention depends on the type of emulsions to be used (e.g., halogen composition), the kind or use of light-sensitive materials to be used, the contrast of emulsions to be used, etc., and it is preferably 100:1 to 1:100, more preferably 10:1 to 1:10. The total amount of silver coated is preferably 0.5 to 10 g/m$^2$.

There are several possible stratum constructions of the photographic element of this invention, for example, (1) a construction wherein an emulsion layer containing photosensitive silver halide grains and internally fogged silver halide grains and a protecting layer are provided on a support in this order, (2) the construction of (1) described above, wherein an emulsion layer containing photosensitive silver halide grains is further provided between the emulsion layer and the protecting layer, and (3) a construction wherein an emulsion layer containing internally fogged silver halide grains, an emulsion layer containing photosensitive silver halide grains and a protecting layer are provided on a support in this order.

These stratum constructions may be provided on a single side or both sides of a support.

The protecting layer of the silver halide photographic light-sensitive material of this invention is one which comprises a hydrophilic colloids. Examples of such hydrophilic colloid are those described earlier. The protecting layer may be of a single layer or a multi layer.

Matting agents and/or smoothing agents may be added to an emulsion layer or a protecting layer, preferably to the protecting layer of the silver halide photographic light-sensitive material of this invention. Examples of the matting agents include organic compounds such as water dispersible vinyl polymers, e.g., polymethylmethacrylate, or inorganic compounds such as silver halides, strontium sulfate, barium sulfate, etc., having particles of a suitable diameter (those having a diameter of 0.3 to 5 microns, or a diameter of more than 2 times, especially more than 4 times the thickness of the protecting layer. Like matting agents, smoothing agents not only aid in the prevention of the problems due to adhesion, but also improve the friction properties which affect its adaptability to the camera during motion picture photography or to the projector during projection. Specific examples of the smoothing agents include liquid paraffins, waxes such as esters of higher aliphatic acids, polyfluorinated hydrocarbons or derivatives thereof, silicones such as polyalkylpolysiloxane, polyarylpolysiloxane, polyalkylarylpolysiloxane, or alkyleneoxide addition derivatives thereof.

The silver halide photographic materials of this invention may contain optionally an antihalation layer, an interlayer, a filter layer, etc.

The silver halide emulsion layers and other hydrophilic colloid layers of the photographic materials of this invention may be hardened by suitable hardeners. Examples of such hardeners include vinyl sulfonyl compounds as described in Japanese Patent Public Disclosure Nos. 76025/1978, 76026/1978 and 77619/1978; those having an active halogen atom; dioxane derivatives; and oxypolysaccharides such as oxystarch.

The silver halide emulsion layers may contain other addenda, e.g., lubricants, sensitizers, light absorptive dyes, plasticizers, etc.

The hydrophilic colloid layers used in this invention may contain various water soluble dyes, as a filter dye, or for the purpose of preventing irradiation, halation, etc. Examples of such dyes include oxonol dyes, hemioxonal dyes, styryl dyes, merocyanine dyes, cyanine dyes and azo dyes. Among these dyes, oxonol dyes, hemioxonol dyes and merocyanine dyes are particularly useful.

When dyes or ultraviolet light absorbing agents are contained in the hydrophilic colloid layer of the light-sensitive materials of this invention, a cationic polymer or the like may be used as a mordant.

The light-sensitive materials of this invention may contain surface active agents for various purposes. Depending on the specific purposes, any of nonionic, ionic or ampholytic surface active agents can be used. Examples of such surface active agents include polyoxyalkylene derivatives, ampholytic amino acids (including sulfobetaines), etc. Such surface active agents are described in U.S. Pat. Nos. 2,600,831; 2,271,622; 2,271,623; 2,275,727; 2,787,604; 2,816,920; and 2,739,891; and Belgian Pat. No. 652,862.

The photographic silver halide emulsions used in the light-sensitive materials of this invention may spectrally be sensitized by sensitizing dyes to blue light having relatively long wavelength, green light, red light or infra-red light. Examples of such sensitizing dyes include cyanine dyes, merocyanine dyes, complex cyanine dyes, complex merocyanine dyes, holopolar cyanine dyes, styryl dyes, hemicyanine dyes, oxonol dyes, hemioxonol dyes, etc. The sensitizing dyes, are used in this invention in a similar concentration to that used in conventional negative silver halide emulsions. Especially, it is advantageous to use the sensitizing dyes in such concentration that the inherent sensitivity of the silver halide emulsion is not substantially lowered. For example, the sensitizing dyes may be used in the range of about $1.0 \times 10^{-5}$ to about $5 \times 10^{-4}$ mole, preferably about $4 \times 10^{-5}$ to about $2 \times 10^{-4}$ mole per one mole of silver halide.

The photographic emulsion layers and other layers of the photographic light-sensitive materials of this invention are coated on one or both sides of a flexible support. Examples of suitable supports include films of synthetic polymers such as cellulose acetate, cellulose butyrate acetate, polystyrene, polyethyleneterephthalate, etc., or paper having coated or laminated thereon a baryta layer, α-olefin polymer (e.g., polyethylene, polypropyrene, ethylene-butene copolymer), etc.

The hydrophilic colloid layers including the photographic emulsion layers of this invention may be applied on a support or other layer by various conventional coating methods such as dipping, roll coating, curtain coating, extrusion coating, etc.

This invention may be applied to any photographic light-sensitive material which requires high sensitivity or high contrast, for example, X-ray photographic light-sensitive materials, Lith-type photographic light-sensitive materials, black-and-white negative photographic light-sensitive materials, color negative light-sensitive materials, color paper light-sensitive materials, etc. This invention may also be applied to diffusion transfer light-sensitive materials in which undeveloped silver halide is dissolved and the silver ion is precipitated in an image receiving layer adjacent to the silver halide emulsion layer to form a positive image, or to color diffusion transfer light-sensitive materials.

For the photographic treatment of the photographic light-sensitive materials of this invention, there may be used any of conventional methods and processing solutions as described in Research Disclosure, No. 176, (1978), pages 28 to 30 (RD-17643). These treatments may be a black-and-white photographic processing in which a silver image is formed or a color photographic processing in which a color image is formed.

The processing temperature is usually in the range of 18° C. to 50° C., although a temperature lower than 18° C. or higher than 50° C. may also be selected.

For example, the developing bath used in the black-and-white processing may contain developing agents commonly known. Examples of such developing agents include dihydroxybenzenes (e.g. hydroquinone), 3-pyrazolidones (e.g., 1-phenyl-3-pyrazolidone), aminophenols (e.g., N-methyl-p-aminophenol), and mixtures thereof. The photographic light-sensitive materials of this invention may be processed in the developing solution as described in Japanese Patent Public Disclosure No. 78535/1982, which contains imidazoles as a silver halide solvent. The developing solution as described in Japanese Patent Public Disclosure No. 37643/1983, which contains a silver halide solvent and addenda such as indazole or triazole, may also be used. Usually, the developing solutions which can be used for the processing of the photographic materials of this invention further contain preservatives, alkali agents, pH buffers, antifoggants and, if necessary, may further contain dissolving aids, toning agents, development accelerators, surface active agents, defoaming agents, water-softening agents, hardeners, viscosity-imparting agents, etc.

The so-called "Lith-type" development processing may be applied to the photographic emulsion of this invention. By "Lith-type" development processing is meant one in which dihydroxybenzenes are usually used as a developing agent and a developing step is conducted in an infectious manner at a low sulfite ion concentration in order to give photographical reproduction of line images or halftone dot images (Details are described in Mason, Photographic Processing Chemistry, (1966), pages 163 to 165).

A special type development may also be applied to the photographic materials of this invention, in which a developing agent is contained in the photographic materials, for example, in the emulsion layer and the photographic materials is processed in an aqueous alkaline solution. Among developing agents, the hydrophobic one can be contained in the emulsion layer by the methods as described in Research Disclosure, No. 169 (RD-16928), U.S. Pat. No. 2,739,890, British Pat. No. 813,253 or West German Pat. No. 1,547,763. Such development processing may be combined with a processing for stabilizing silver salt with thiocyanates.

As fixing agents, those having a commonly used formulation can be employed. Examples of such fixing agents which can be used include, in addition to thiosulfates and thiocyanates, organic sulfur-containing compounds which are useful as a fixing agent. The fixing agents used in this invention may contain water soluble aluminum salts as a hardener.

This invention will now be explained in more detail with reference to the following Examples.

EXAMPLE 1

(1) Preparation of a photosensitive silver halide emulsion

According to the conventional ammonia method, silver nitrate was reacted with potassium bromide and potassium iodide to prepare an emulsion containing silver bromoiodide (Ag I: 6 mole %) grains having a mean diameter of 1.0 micron. The grains were chemically sensitized by gold-sulfur sensitization using chloroauric acid and sodium thiosulfate and then washed by the conventional flocculation method. To the grains, 4-hydroxy-6-methyl-1,3,3a,7-tetraazaindene was added as a stabilizer to prepare a photosensitive silver bromoiodide emulsion A-1.

(2) Preparation of internally fogged silver halide emulsion

An aqueous solution of silver halide and an aqueous solution of potassium bromide and sodium chloride were simultaneously added to a 2 percent by weight gelatin solution in water at 55° C. with stirring to prepare core grains. The temperature of this mixture was raised up to 75° C. and sodium hydroxide and silver nitrate were added in an appropriate amount, whereafter the mixture was kept for 15 minutes for ripening to prepare fog centers on the core grains. The temperature was lowered to 55° C. and acetic acid and potassium bromide were added to adjust the pH value and the pAg value to the initial ones. Further, a silver nitrate solution and a solution of potassium bromide and sodium chloride in water were simultaneously added thereto, desalted by conventional flocculation method and then dispersed again in a gelatin solution to prepare an internally fogged silver chlorobromide emulsion B-1 (AgCl: 10 mole %, mean diameter of the grains: 0.37 micron).

(3) Preparation of Coating samples

The internally fogged silver halide emulsion B-1 was divided into five portions. Compounds 4 and 23 of this invention and Comparative Compounds (a) and (b) described below were added to the first, second, third and fourth portions respectively in the amount of $2.2 \times 10^{-3}$ mole per one mole of silver halide and no compound was added to the remaining portion.

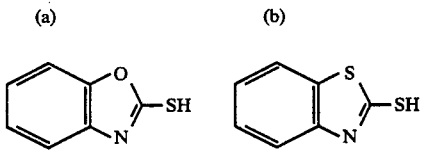

Both compounds (a) and (b) are described in U.S. Pat. No. 3,397,987.

Oxamonomethinecyanine dye, polyethyleneoxide and a vinylsulfone hardener were added to each of the photosensitve silver halide emulsion A-1, a mixed emulsion of the photosensitive silver halide emulsion A-1 and the internally fogged silver halide emulsion B-1 at a A-1 to B-1 silver halide mole ratio of 5:1, and a mixed emulsion of the photosensitive silver halide emulsion A-1 and each of the internally fogged silver halide emulsions B-1 to which various compounds had previously been added at a A-1 to B-1 silver halide mole ratio of 5:1, to prepare coating liquids. Each of these coating liquids was uniformly coated on both sides of a polyester support previously undercoated. A surface protecting layer comprising mainly a gelatin solution in water was provided on each of the coatings to prepare Coating samples 1 to 6 as shown in Table 1. In all samples, the amount of silver coated was 5.2 g/m$^2$, the amount of gelatin coated in the emulsion layer was 2.1 g/m$^2$ and the amount of gelatin coated in the protecting layer was 1.2 g/m$^2$.

(4) Evaluation of Coating samples

Coating samples 1 to 6 were exposed to light from both sides thereof through a wedge, developed in the developing solution A at 35° C. for 25 seconds, fixed, washed with water, dried and then, sensitometry was conducted.

| Formulation of the developing solution A | |
|---|---|
| Potassium hydroxide | 29.14 g |
| Glacial acetic acid | 10.96 g |
| Potassium sulfite | 44.20 g |
| Sodium bicarbonate | 7.50 g |
| Boric acid | 1.00 g |
| Diethyleneglycol | 28.96 g |
| Ethylenediaminetetraacetic acid | 1.67 g |
| 5-Methylbenztriazole | 0.06 g |
| 5-Nitroindazole | 0.25 g |
| Hydroquinone | 30.00 g |
| 1-Phenyl-3-pyrazolidone | 1.50 g |
| Glutaraldehyde | 4.93 g |
| Sodium metabisulfite | 12.60 g |
| Potassium bromide | 7.00 g |
| Water to | 1 l |
| pH | 10.25 |

Separately, Coating samples 1 to 6 were kept at 50° C. and relative humidity of 80% for 1.5 days and then, exposed, processed in the developing solution A in a similar manner, and relative sensitivity was measured.

Further, Coating samples 1 to 6 were processed through an automatic developing processor (manufactured by FUJI PHOTO FILM CO., LTD., RG Automatic developing processor, the developing solution A was used) through which photographic materials had previously been processed so as to put the processor into a stable state. The degrees of irregular stains formed on the processed samples were evaluated according to the following criteria: 1 . . . strikingly formed, 2 . . . difficult for practical use, 3 . . . there is a problem for practical use, 4 . . . formed but no problem for practical use, 5 . . . not formed. The results are summarized in Table 1.

TABLE 1

| | Sample No. | Emulsion | Compound added to emulsion B-1 | Photographic properties | | | | Relative sensitivity after high temperature and humidity** | Irregular stains |
|---|---|---|---|---|---|---|---|---|---|
| | | | | Relative sensitivity* | Fog density | Gamma | D max. | | |
| Comparative sample | 1 | (A-1) alone | — | 100 | 0.05 | 1.7 | 2.7 | 100 | 5 |
| Comparative sample | 2 | (A-1) + (B-1) | — | 115 | 0.08 | 3.3 | 3.2 | 115 | 1 |
| Comparative sample | 3 | " | Comparative compound (a) | 100 | 0.04 | 2.8 | 3.2 | 55 | 1 |

TABLE 1-continued

| Sample No. | Emulsion | Compound added to emulsion B-1 | Relative sensitivity* | Fog density | Gamma | D max. | Relative sensitivity after high temperature and humidity** | Irregular stains |
|---|---|---|---|---|---|---|---|---|
| Comparative sample 4 | " | Comparative compound (b) | 95 | 0.03 | 2.6 | 3.1 | 50 | 1 |
| This invention 5 | " | Compound 4 | 120 | 0.04 | 3.4 | 3.2 | 115 | 4 |
| This invention 6 | " | Compound 23 | 120 | 0.03 | 3.4 | 3.1 | 120 | 4 |

*Calculated by taking the sensitivity value of Sample No. 1 as 100.
**Calculated by taking the sensitivity value of Sample No. 1 before being kept under the conditions of high temperature and high humidity as 100.

Table 1 shows the following:

Comparative sample 2, as compared with Comparative sample 1, is better in sensitivity, gamma and maximum density but shows high fog density and is much inferior in irregular stains formed in the processing by the automatic developing processor. Comparative samples 3 and 4 which contain Comparative Compounds (a) and (b) described in U.S. Pat. No. 3,397,987, respectively, are better in fog density, which is one of the problems of Comparative sample 2, but the samples 3 and 4 are lower in sensitivity and gamma, especially in sensitivity after standing under conditions of high temperature and moisture and show no improvement in irregular stains caused by the automatic developing processor. In contrast, Samples 5 and 6 of this invention, which contain Compounds 4 and 23, respectively, are superior to Comparative samples in photographic properties (i.e. sensitivity, fog density, gamma and maximum density) and the sensitivity after standing under conditions of high temperature and moisture, and further show no serious irregular stains caused by the automatic developing processor from the point of practical use, which shows the outstanding effects of this invention.

EXAMPLE 2

(1) Preparation of photosensitive silver halide emulsion

Procedures similar to those of Example 1 were repeated to prepare a photosensitive silver halide emulsion A-2 comprising silver bromoiodide grains (AgI: 4 mole %; mean diameter of the grain: 1.0 micron)

(2) Preparation of internally fogged silver halide emulsion

In a manner similar to that of Example 1 as described in U.S. Pat. No. 2,592,250, there was prepared a silver halide emulsion comprising silver bromochloride grains (AgCl: 2 mole %, mean diameter of the grains: 0.3 micron) having high internal-photosensitivity, which was then exposed to light to prepare an internally fogged silver bromochloride emulsion B-2.

(3) Preparation of Coating sample

The internally fogged silver halide emulsion B-2 was divided into eight portions. Compounds 23, 10, 16, 18, 22, 14 and 31 were added to the seven portions, respectively, in the amount of $2.2 \times 10^{-3}$ mole per one mole of silver halide contained in the emulsion but no compound was added to the remaining portion.

The 4,5-dihydro-2,4-diphenyl-5-phenylimino-1H-triazolium inner salt salicylate and a triazine hardener were added to each of the photosensitive silver halide emulsions A-2, a mixed emulsion of the photosensitive silver halide emulsion A-2 and the internally fogged silver halide emulsion B-2 at a A-2 to B-2 silver halide mole ratio of 5:1, and mixed emulsions of the photosensitive silver halide emulsion A-2 and each of the internally fogged silver halide emulsions B-2 to which various compounds had previously been added at a A-2 to B-2 silver halide mole ratio of 5:1, to prepare coating liquids.

Each of these coating liquids was uniformly coated on both sides of a polyester support previously undercoated. A surface protecting layer comprising mainly a gelatin solution in water was provided on each of the coatings to prepare Coating samples 7 to 15 as shown in Table 2. In all samples, the amount of silver coated was 5.2 g/m², the amount of gelatin coated in the emulsion layer was 2.1 g/m² and the amount of gelatin coated in the protecting layer was 1.2 g/m².

(4) Evaluation of Coating samples

The same procedures as in Example were repeated. The results are summarized in Table 2.

TABLE 2

| Sample No. | Emulsion | Compound added to emulsion B-2 | Relative sensitivity* | Fog density | Gamma | D max. | Relative sensitivity after high temperature and humidity** | Irregular stains |
|---|---|---|---|---|---|---|---|---|
| Comparative sample 7 | (A-2) alone | — | 100 | 0.04 | 1.9 | 2.8 | 105 | 5 |
| Comparative sample 8 | (A-2) + (B-2) | — | 110 | 0.08 | 3.4 | 3.5 | 115 | 2 |
| This invention 9 | " | Compound 23 | 115 | 0.04 | 3.5 | 3.4 | 120 | 4–5 |
| This invention 10 | " | Compound 10 | 118 | 0.03 | 3.6 | 3.5 | 118 | 5 |
| This invention 11 | " | Compound 16 | 115 | 0.04 | 3.5 | 3.4 | 115 | 4–5 |
| This invention 12 | " | Compound 18 | 118 | 0.03 | 3.5 | 3.5 | 120 | 4–5 |
| This invention 13 | " | Compound 22 | 115 | 0.04 | 3.6 | 3.5 | 115 | 5 |
| This invention 14 | " | Compound 14 | 112 | 0.05 | 3.5 | 3.4 | 115 | 5 |
| This invention 15 | " | Compound 31 | 118 | 0.03 | 3.6 | 3.5 | 118 | 5 |

TABLE 2-continued

| Sample No. | Emulsion | Compound added to emulsion B-2 | Relative sensitivity* | Fog density | Gamma | D max. | Relative sensitivity after high temperature and humidity** | Irregular stains |
|---|---|---|---|---|---|---|---|---|
| invention | | | | | | | | |

*Calculated by taking the sensitivity value of Sample No. 7 as 100.
**Calculated by taking the sensitivity value of Sample No. 7 before being kept under the conditions of high temperature and high humidity as 100.

Table 2 shows that the outstanding effects of this invention can also be attained by the samples 9 to 15 of this invention. Table 2 also shows that various compounds represented by the formula (I) can be used to advantage in this invention.

EXAMPLE 3

(1) Preparation of photosensitive silver halide emulsion

Procedures similar to those of Example 1 were repeated to prepare a photosensitive silver halide emulsion A-3 comprising silver bromoiodide grains (AgI: 4 mole %, mean diameter of the grains: 1.0 micron)

(2) Preparation of internally fogged silver halide emulsion

In a manner similar to that of Example 1 as described in U.S. Pat. No. 2,592,250, there was prepared a silver halide emulsion comprising silver bromochloride grains (AgCl: 10 mole %; mean diameter of the grains: 0.3 micron) having high internal-photosensitivity. 4,5-Dihydro-2,4-diphenyl-5-phenylimino-1H-triazolium inner salt salicylate was added to this emulsion, which was then exposed to light to prepare an internally fogged silver bromochloride emulsion B-3.

(3) Preparation of Coating samples

The internally fogged silver halide emulsion B-3 was divided into five portions. Compounds 10, 11 and 23 of this invention, and Comparative compound (C) of the following formula were added to four portions, respectively, in the amount of $2.2 \times 10^{-3}$ mole per one mole of silver halide contained in the emulsion but no compound was added to the remaining portion.

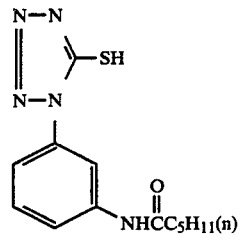
(C)

Oxamonomethine dye, polyethyleneoxide and a vinylsulfone hardener were added to each of the photosensitive silver halide emulsion A-3, a mixed emulsion of the photosensitive silver halide emulsion A-3 and the internally fogged silver halide emulsion B-3 at a A-3 to B-3 silver halide mole ratio of 5:1, and mixed emulsions of the photosensitive silver halide emulsion A-2 and each of the internally fogged silver halide emulsions B-2 to which various compounds had previously been added at a A-3 to B-3 silver halide mole ratio of 5:1, to prepare coating liquids.

Each of these coating liquids was uniformly coated on both sides of a polyester support previously undercoated. A surface protecting layer comprising mainly a gelatin solution in water was provided on each of the coatings to prepare Coating samples 16 to 21 as shown in Table 3. In all samples, the amount of silver coated was 5.2 g/m², the amount of gelatin coated in the emulsion layer was 2.1 g/m² and the amount of gelatin coated in the protecting layer was 1.2 g/m².

(4) Evaluation of Coating samples

The same procedures as in Example 1 were repeated. The results are summarized in Table 3.

TABLE 3

| | Sample No. | Emulsion | Compound added to emulsion B-3 | Relative sensitivity* | Fog density | Gamma | D max. | Relative density after high temperature and humidity** | Irregular stains |
|---|---|---|---|---|---|---|---|---|---|
| Comparative sample | 16 | (A-3) alone | — | 100 | 0.03 | 2.0 | 2.8 | 102 | 5 |
| Comparative sample | 17 | (A-3) + (B-3) | — | 110 | 0.06 | 3.5 | 3.5 | 113 | 2 |
| Comparative sample | 18 | " | Comparative compound (c) | 105 | 0.03 | 3.5 | 3.6 | 40 | 4 |
| This invention | 19 | " | Compound 10 | 115 | 0.02 | 3.6 | 3.5 | 117 | 5 |
| This invention | 20 | " | Compound 11 | 115 | 0.02 | 3.6 | 3.5 | 115 | 5 |
| This invention | 21 | " | Compound 23 | 115 | 0.02 | 3.5 | 3.5 | 117 | 5 |

*Calculated by taking the sensitivity value of Sample No. 16 as 100.
**Calculated by taking the sensitivity value of Sample No. 16 before being kept under the conditions of high temperature and high humidity as 100.

Table 3 shows that the same effects as in Example 1 and 2 can also be attained in this Example 3.

Samples 19, 20 and 21 of this invention show much better improvement in stains formed in the processing by the automatic developing processor than Comparative sample 18 containing Comparative compound (c) which is described as the best compound in U.S. Pat.

No. 3,397,987, and further the samples of this invention are superior in sensitivity, especially that after being kept under conditions of high temperature and high humidity.

What we claim is:

1. A silver halide photographic light-sensitive material comprising a support having coated thereon at least one silver halide emulsion layer and a surface protecting layer, said silver halide photographic light-sensitive material comprising unfogged surface latent image silver halide grains and internally fogged silver halide grains, said internally fogged silver halide grains having adsorbed thereon at least one compound represented by the formula (I):

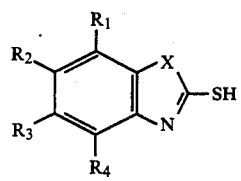

wherein X represents —O—, —NH— or —S—, $R_1$, $R_2$, $R_3$ and $R_4$ represent hydrogen atom or a substituent, and at least one of $R_1$, $R_2$, $R_3$ and $R_4$ is substituted or unsubstituted alkyl or aryl group having up to 13 carbon atoms, which is bonded directly or through a divalent linkage group, to the aromatic nucleus, in an amount sufficient to inhibit irregular stains formed in the processing of the silver halide photographic light-sensitive material by an automatic developing processor and sufficient to stabilize the photographic properties of the material when stored under conditions of high temperature and moisture.

2. The silver halide photograhic light-sensitive material of claim 1, wherein X of the formula (I) represents —NH—.

3. The silver halide photographic light-sensitive material of claim 1, wherein $R_1$, $R_2$, $R_3$ and $R_4$ individually represent hydrogen or halogen atom, alkyl, aryl, alkoxy, aryloxy, sulfonyl, sulfonamido, sulfamoyl, carbamoyl, amido, ureido, arylcarbonylamino, aryloxycarbonylamino, alkylcarbonylamino, alkoxycarbonylamino, arylcarbonyl, aryloxycarbonyl, alkylcarbonyl, alkyloxycarbonyl, arylaminocarbonyloxy, alkylaminocarbonyloxy, cyano, alkylthio or arylthio group.

4. The silver halide photographic light-sensitive material of claim 1, wherein the divalent linkage group is selected from the group consisting of amido, sulfonamido, ureido, ether, thioether, sulfonyl, carbonyl, urethane, carbamoyl and sulfamoyl linkages.

5. The silver halide photographic light-sensitive material of claim 1, wherein the compound represented by the formula (I) is used in an amount of $1 \times 10^{-5}$ to $1 \times 10^{-1}$ mole per mole of the internally fogged silver halide grains.

6. The silver halide photographic light-sensitive material of claim 1, wherein the compound represented by the formula (I) is used in an amount of $1 \times 10^{-4}$ to $1 \times 10^{-2}$ mole per mole of the internally fogged silver halide grains.

7. The silver halide photographic light-sensitive material of claim 1, wherein the sensitivity of the photosensitive silver halide grains is at least ten times higher than that of the internally fogged silver halide grains.

8. The silver halide photographic light-sensitive material of claim 1, wherein the sensitivity of the photosensitive silver halide grains is at least one hundred times higher than that of the internally fogged silver halide grains.

9. The silver halide photographic light-sensitive material of claim 1, wherein the photosensitive silver halide grains are of the surface latent image type.

10. The silver halide photographic light-sensitive material of claim 9, wherein the surface latent image type grains are silver bromoiodide containing 0.5 to 10 mole % of silver iodide.

11. The silver halide photographic light-sensitive material of claim 1, wherein the average size of the internally fogged silver halide grains is from 0.05 micron to 1.0 microns.

12. The silver halide photographic light-sensitive material of claim 1, wherein the weight ratio of the photosensitive silver halide grains to the internally fogged silver halide grains is 100:1 to 1:100.

13. The silver halide photographic light-sensitive material of claim 1, wherein an emulsion layer containing the photosensitive silver halide grains and the internally fogged silver halide grains and the protecting layer are provided on the support in this order.

14. The silver halide photographic light-sensitive material of claim 13, wherein an emulsion layer containing the photosensitive silver halide grains is further provided between the emulsion layer and the protecting layer.

15. The silver halide photographic light-sensitive material of claim 1, wherein an emulsion layer containing the internally fogged silver halide grains, an emulsion layer containing photosensitive silver halide grains and the protecting layer are provided on the support in this order.

* * * * *